(12) United States Patent
Moore

(10) Patent No.: US 7,538,860 B2
(45) Date of Patent: May 26, 2009

(54) SYSTEM AND METHOD FOR DETERMINATION OF THE REFLECTION WAVELENGTH OF MULTIPLE LOW-REFLECTIVITY BRAGG GRATINGS IN A SENSING OPTICAL FIBER

(75) Inventor: Jason P. Moore, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 136 days.

(21) Appl. No.: 11/840,363

(22) Filed: Aug. 17, 2007

(65) Prior Publication Data

US 2009/0046276 A1    Feb. 19, 2009

(51) Int. Cl.
*G01L 1/24* (2006.01)
(52) U.S. Cl. .................................... 356/35.5; 356/478
(58) Field of Classification Search ............... 356/35.5, 356/478; 250/227.19, 227.27
See application file for complete search history.

(56) References Cited

U.S. PATENT DOCUMENTS

| | | | |
|---|---|---|---|
| 5,675,674 A * | 10/1997 | Weis | 385/12 |
| 5,798,521 A | 8/1998 | Froggatt | |
| 5,844,235 A | 12/1998 | Tachikawa et al. | |
| 5,867,258 A * | 2/1999 | Frederick et al. | 356/35.5 |
| 5,943,124 A | 8/1999 | Haigh | |
| 5,991,026 A * | 11/1999 | Kluth et al. | 356/478 |
| 6,008,487 A | 12/1999 | Tachikawa et al. | |
| 6,201,237 B1 | 3/2001 | Berkey et al. | |
| 6,204,920 B1 * | 3/2001 | Ellerbrock et al. | 356/477 |
| 6,376,830 B1 | 4/2002 | Froggatt et al. | |
| 6,495,819 B1 | 12/2002 | Cerwin et al. | |
| 6,566,648 B1 | 5/2003 | Froggatt | |
| 6,856,400 B1 | 2/2005 | Froggatt | |
| 6,876,786 B2 | 4/2005 | Chliaguine et al. | |
| 6,900,897 B2 | 5/2005 | Froggatt | |
| 6,940,601 B2 | 9/2005 | Englund et al. | |
| 7,042,573 B2 | 5/2006 | Froggatt | |
| 7,064,839 B2 | 6/2006 | Bussard et al. | |
| 7,119,325 B2 | 10/2006 | Pieterse et al. | |
| 2001/0013934 A1 * | 8/2001 | Varnham et al. | 356/478 |
| 2002/0041722 A1 * | 4/2002 | Johnson et al. | 385/12 |
| 2004/0067003 A1 | 4/2004 | Chliaguine et al. | |
| 2004/0196467 A1 | 10/2004 | Froggatt | |
| 2005/0219512 A1 | 10/2005 | Froggatt et al. | |
| 2006/0164627 A1 | 7/2006 | Froggatt et al. | |
| 2006/0204165 A1 | 9/2006 | Froggatt | |
| 2007/0009197 A1 | 1/2007 | Poland et al. | |

* cited by examiner

*Primary Examiner*—Tarifur Chowdhury
*Assistant Examiner*—Jonathon D Cook

(57) ABSTRACT

A system and method for determining a reflection wavelength of multiple Bragg gratings in a sensing optical fiber comprise: (1) a source laser; (2) an optical detector configured to detect a reflected signal from the sensing optical fiber; (3) a plurality of frequency generators configured to generate a signal having a frequency corresponding to an interferometer frequency of a different one of the plurality of Bragg gratings; (4) a plurality of demodulation elements, each demodulation element configured to combine the signal produced by a different one of the plurality of frequency generators with the detected signal from the sensing optical fiber; (5) a plurality of peak detectors, each peak detector configured to detect a peak of the combined signal from a different one of the demodulation elements; and (6) a laser wavenumber detection element configured to determine a wavenumber of the laser when any of the peak detectors detects a peak.

14 Claims, 8 Drawing Sheets

SYSTEM AND METHOD FOR DETERMINATION OF THE REFLECTION WAVELENGTH OF MULTIPLE LOW-REFLECTIVITY BRAGG GRATINGS IN A SENSING OPTICAL FIBER

FIELD OF THE INVENTION

The present invention generally relates to the use of in-fiber Bragg gratings sensors and, more particularly, relates to systems and methods for determining a reflection wavelength of multiple low-reflectivity Bragg gratings in a sensing optical fiber.

BACKGROUND OF THE INVENTION

A Bragg grating is a periodic variation in the refractive index in a small section of optical fiber cable. As light propagates along the fiber, a very narrow range of wavelengths is reflected by the Bragg grating while all other wavelengths are transmitted through the grating. The center of this reflected band is called the Bragg wavelength. In-fiber Bragg gratings sensors have been utilized as measuring devices for strain, temperature, pressure, and chemical presence, as examples. Typically, the measurements are based on identifying the peak reflection wavelength of a grating or interrogating the reflection or transmission wavelength spectrum of a grating, and then inferring strain effects based on the shifting of each grating's peak reflection wavelengths or spectra. As strain sensors, the fiber containing Bragg gratings sensors is typically bonded to the surface of a test article or is embedded within the material under test. As the test article is subjected to loading or other strain-inducing phenomena, the fiber experiences an induced strain. The induced strain at a Bragg grating sensor area causes the peak reflection wavelength of that sensor to shift, generally in a linear fashion, in relation to strain. Bragg grating sensor systems typically perform temperature measurements by inferring temperature changes after measuring fiber strain that occurs due to the fiber's coefficient of thermal expansion. Pressure and chemical sensor systems perform similarly, as they typically measure in-fiber Bragg grating sensor strain which is induced through the physical or chemical changes of materials around the sensing fiber. It is to this end that systems have been developed for the purpose of measuring or calculating the peak reflection wavelengths of in-fiber Bragg grating sensors. Because the information from a Bragg grating sensor can directly relate hazardous structural or environmental conditions to the appropriate safety interests and because properties under test can exhibit rapid changes, it is desirable to perform these wavelength measurements as quickly and as numerously as possible while maintaining acceptable accuracy.

Known methods and systems for determination of the spectra and/or the peak reflection wavelengths of multiple Bragg grating sensors in a single fiber use Optical Frequency Domain Reflectometer (OFDR) technology. Current OFDR systems derive wavelength information of Bragg gratings in a single fiber by sampling and storing the reflections from a sensing fiber while sweeping the wavelength of a system source laser. The recorded data is then manipulated through processor-intensive algorithms, such as Discrete Fourier Transforms, data filtering/smoothing, and threshold/peak detection. Such processing adds significant delay in the determination of Bragg grating reflection wavelengths, which in turn delays the measurement data repetition rates.

One known OFDR system and algorithm is capable of interrogating multiple (hundreds) Bragg grating sensors on a single fiber with the nominal wavelengths of the sensors being equal. Prior to the use of OFDR, Bragg grating sensors were interrogated using wavelength division multiplexing (WDM) systems which required the nominal reflection wavelengths of the sensors to be non-equal. WDM systems were also limited in the number of sensors they could interrogate on a single fiber. The OFDR technology allows for the interrogation of several hundred Bragg grating sensors all located on one fiber and all nominally having equal reflection wavelengths. The extensive processing of a large data set and the required analog-to-digital (A/D) conversion rates are the main limitations in the speed of the measurement using OFDR technology Techniques which are less processor-intensive than the current OFDR method exist; however, they are limited in the number of Bragg grating sensors they are able to interrogate from one fiber. Selecting an appropriate Bragg grating sensor system usually involves assigning priority between interrogation speed, sensor number, and measurement accuracy. A system with high data repetition rates as highest priority will usually have a lower sensor quantity capability, reduced accuracy, or both. A system such as the OFDR technology, which is capable of measuring several sensors on one fiber, has high accuracy, but low data repetition rates. The most desirable system is one that combines high speed repetition rates with multiple sensor capability and accuracy comparable with other state-of-the art systems.

One method of interrogating in-fiber Bragg grating sensors using traditional Optical Frequency Domain Reflectometer (OFDR) technology is disclosed in U.S. Pat. No. 6,566,648, issued May 20, 2003, to Froggatt, the contents of which are incorporated herein in their entirety. The method disclosed in Froggatt is capable of measuring many numbers (hundreds) of Bragg grating sensors, but has undesirable processor-intensive algorithms which limit its speed capabilities. Froggatt's OFDR method utilizes a monotonically wavelength sweeping, continuous output, high coherence laser as the source for the sensing fiber and a separate fiber network which contains the necessary fiber optic components to generate calibrated interference fringes which are used to clock the sampling of the sensing fiber reflections through an A/D.

Providing the desired capability (high speed, high sensor number, and high accuracy) has been accomplished by stacking, or paralleling, multiple systems. A WDM-based system, for example, can read several Bragg grating sensors by having multiple source lasers to provide wide bandwidths, or., as is usually instituted, multiple fibers are connected to one system. An OFDR system can provide pseudo-high-speed capability and still interrogate several hundred sensors on one fiber by storing data and deriving measurements in a post-processing fashion. The latter method still does not provide useful measurements in real-time, so the high speed capability is still not completely realized. An effort to improve the processing speed of current OFDR technology through improved processing hardware and software algorithms is underway and has resulted in increased measure speeds; however, the inherent requirement of an OFDR system to sample data and perform Discrete Fourier Transforms and other related algorithms restricts the technology to be limited by A/D conversion speeds and processor speeds.

BRIEF SUMMARY OF THE INVENTION

The object of the present invention is to overcome the aforementioned drawbacks of OFRD-based Bragg grating sensor systems and to provide high interrogation speed, sensor number, and measurement accuracy. The system and method of embodiments of the invention yield a system capable of determining the spectra and/or peak reflection wavelengths of multiple Bragg gratings on a single sensing optical fiber without the use of processor-intensive, post-sampling algorithms. Measurements and determinations are performed in real-time, as the OFDR source laser is swept through its wavelength range, resulting in significantly higher data repetition rates.

In one embodiment of the invention, a system is provided for determining a reflection wavelength of multiple low-reflectivity Bragg gratings in a sensing optical fiber having a broadband reflector and a plurality of the Bragg gratings at different distances from the broadband reflector along a length of the sensing optical fiber. The system comprises: (1) a source laser coupled to the sensing optical fiber; (2) an optical detector coupled to the sensing optical fiber and configured to detect a reflected signal from the sensing optical fiber; (3) a plurality of frequency generators, each frequency generator configured to generate a signal having a frequency corresponding to an interferometer frequency of a different one of the plurality of Bragg gratings; (4) a plurality of demodulation elements, each demodulation element coupled to the optical detector and to a different one of the plurality of frequency generators, each demodulation element configured to combine the signal produced by a different one of the plurality of frequency Generators with the detected signal from the sensing optical fiber; (5) a plurality of peak detectors, each peak detector coupled to a different one of the demodulation elements and configured to detect a peak of the combined signal from a different one of the demodulation elements; and (6) a laser wavenumber detection element coupled to the peak detectors and configured to determine a wavenumber of the laser when any of the peak detectors detects a peak.

In one embodiment of the invention, the plurality of frequency generators each comprise a frequency synthesizer. In an alternative embodiment, the plurality of frequency generators each comprise an optical fiber interferometer, each interferometer comprising two lengths of optical fiber having a difference in length substantially equal to the distance between the broadband reflector and a different one of the plurality of Bragg gratings.

The laser wavenumber detection element may comprise: (1) a reference optical fiber network coupled to the source laser and configured to provide a wavenumber counting signal; (2) a calibrated optical fiber network configured to reflect light from the source laser when the source laser is emitting light at a predetermined frequency; (3) a counter coupled to the reference optical fiber network and the calibrated optical fiber network, the counter being clocked by the wavenumber counting signal and triggered by the reflection of light from the calibrated optical fiber network; and (4) a plurality of registers each register configured to capture and store an output value from the counter when a different one of the peak detectors detects a peak.

The source laser may comprise a high coherence, monotonically wavelength sweeping, continuous output, mode-hop free, fiber-coupled laser.

In one embodiment of the invention, each demodulation element comprises an analog multiplier and a low-pass filter. In an alternative embodiment, each demodulation element comprises an analog mixer and a low-pass filter.

In addition to the system for determining a reflection wavelength of multiple low-reflectivity Bragg gratings in a sensing optical fiber having a broadband reflector and a plurality of the Bragg gratings at different distances from the broadband reflector along a length of the sensing optical fiber as described above, other aspects of the present invention are directed to corresponding methods for determining a reflection wavelength of multiple low-reflectivity Bragg gratings in such a sensing optical fiber.

BRIEF DESCRIPTION OF THE DRAWINGS

Figure 1:
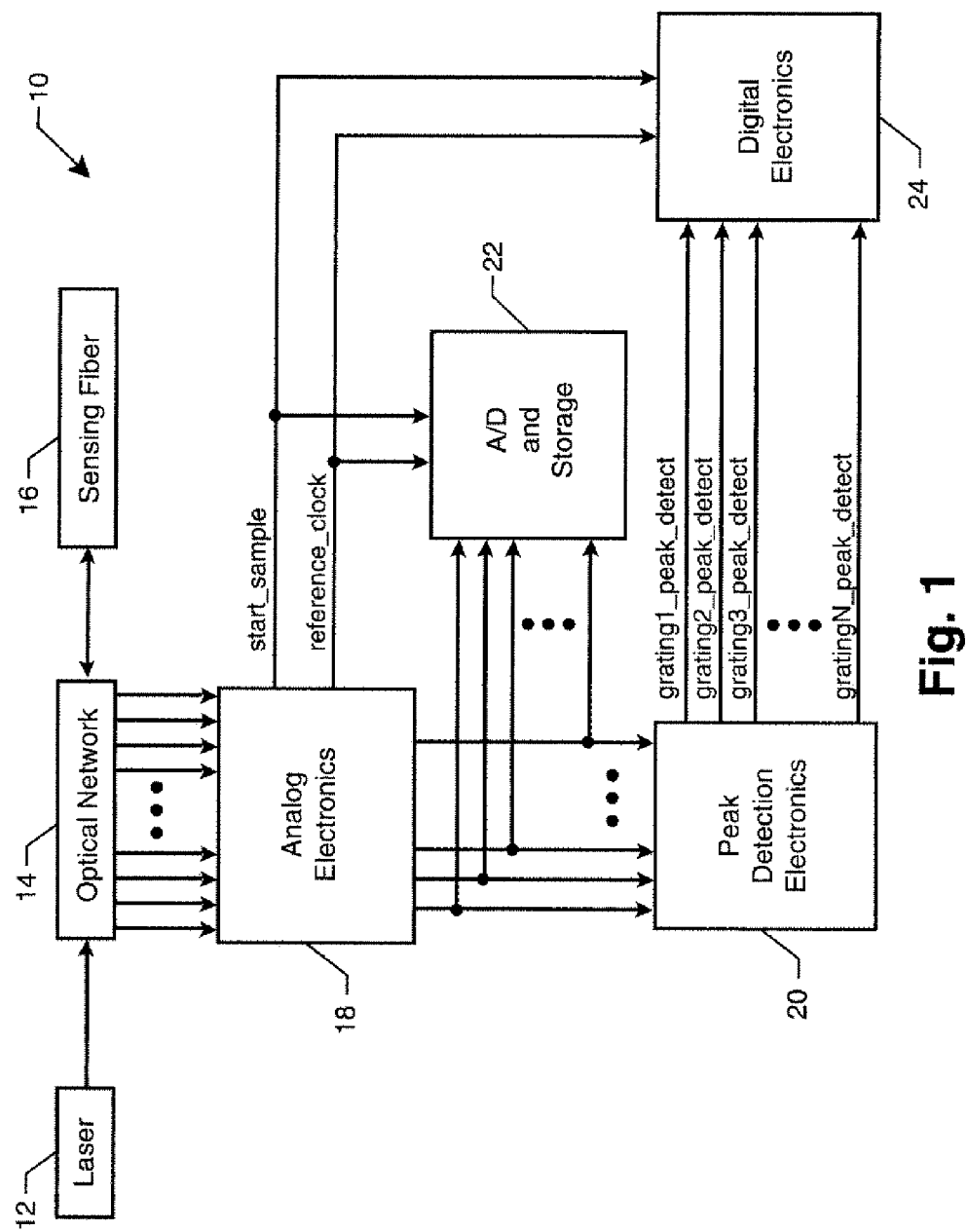
Figure 2:
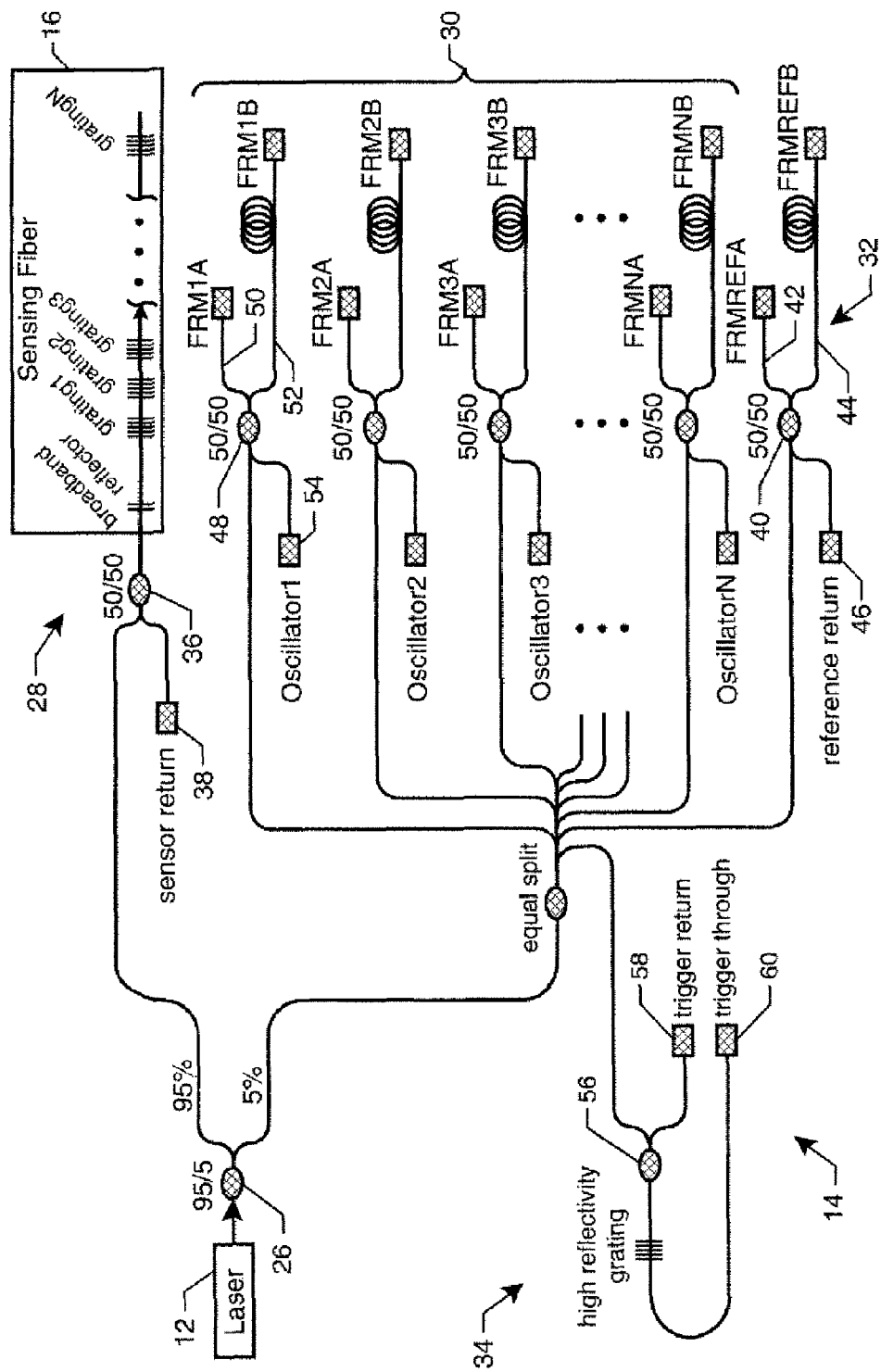
Figure 3:
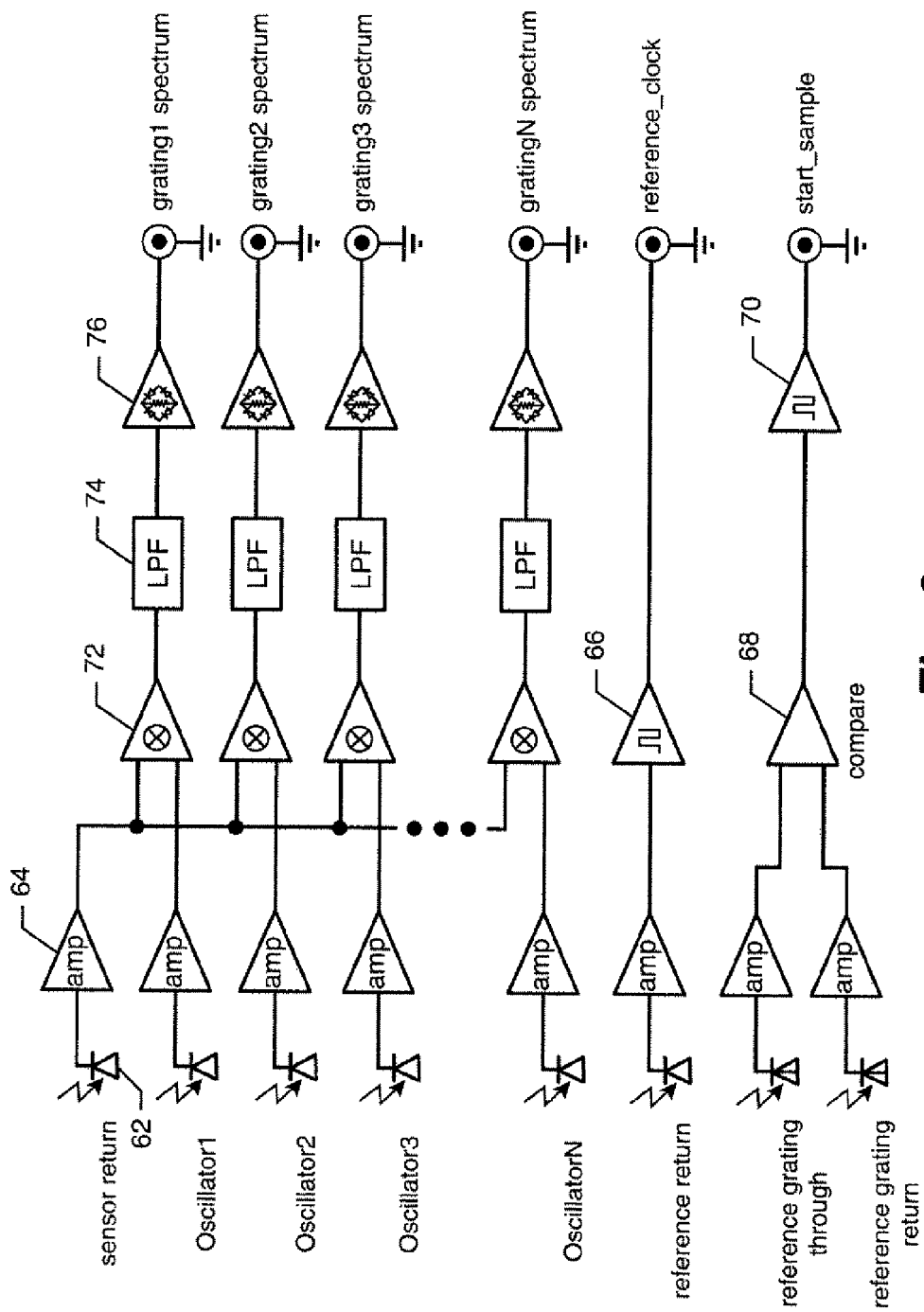
Figure 4:
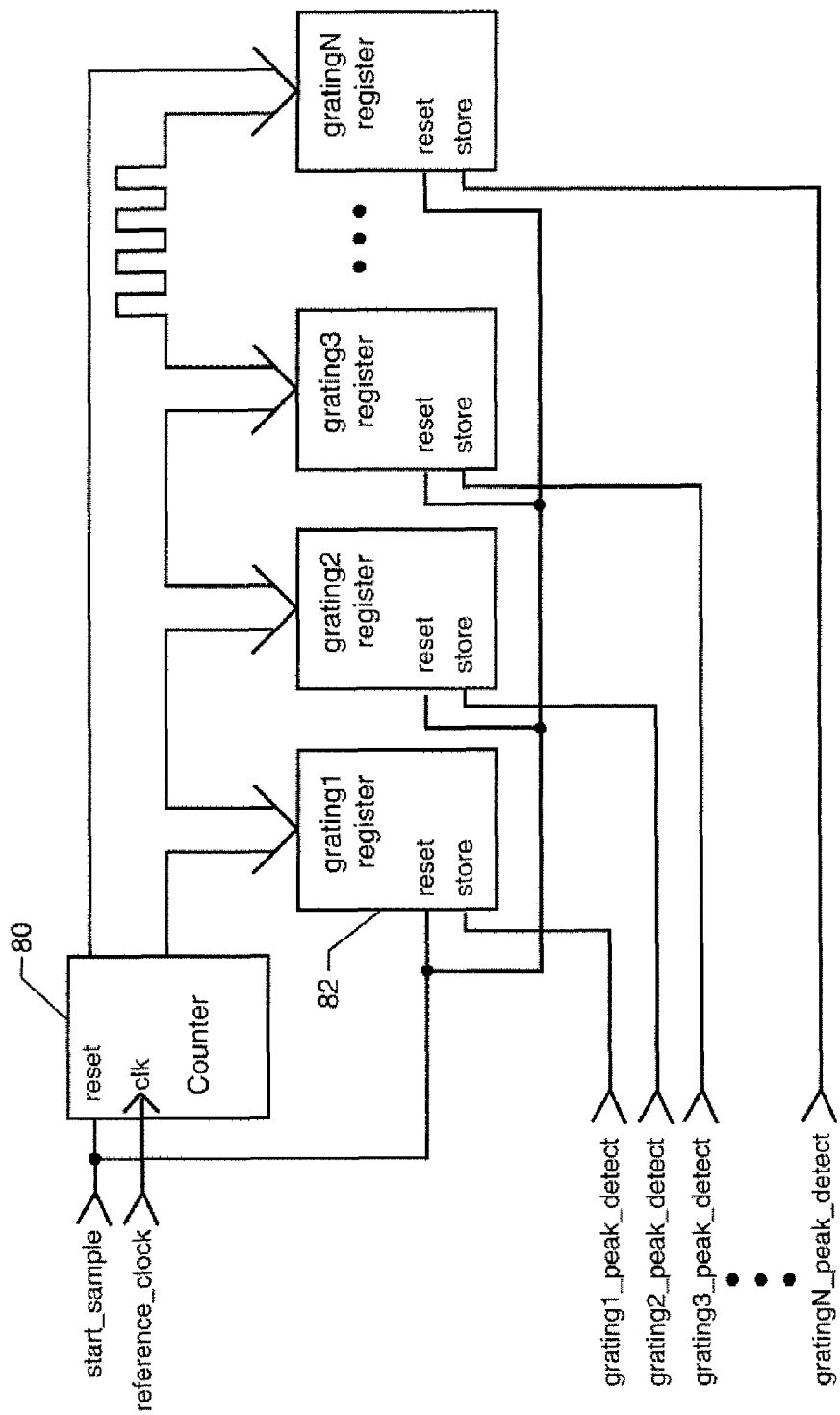
Figure 5:
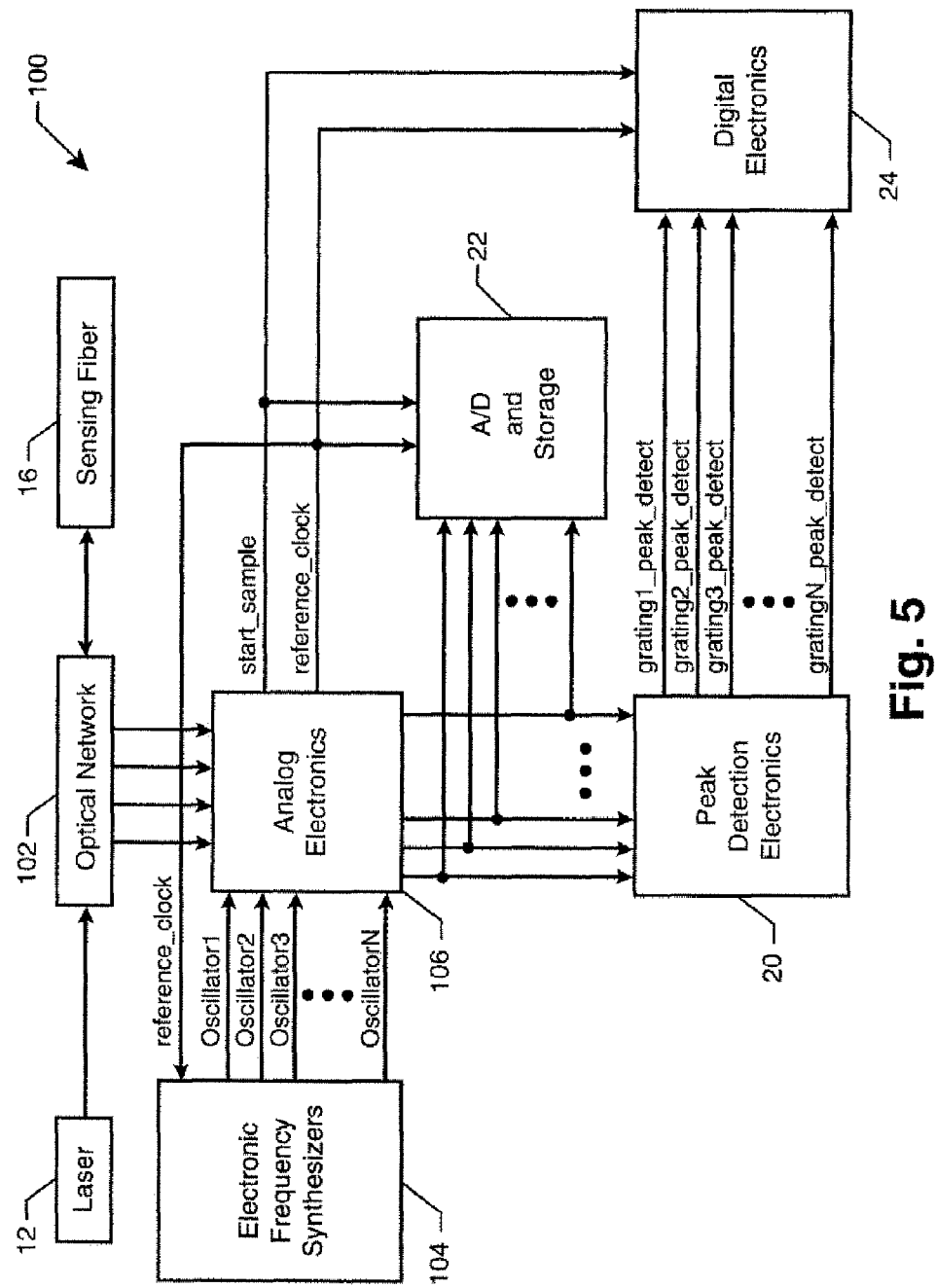
Figure 6:
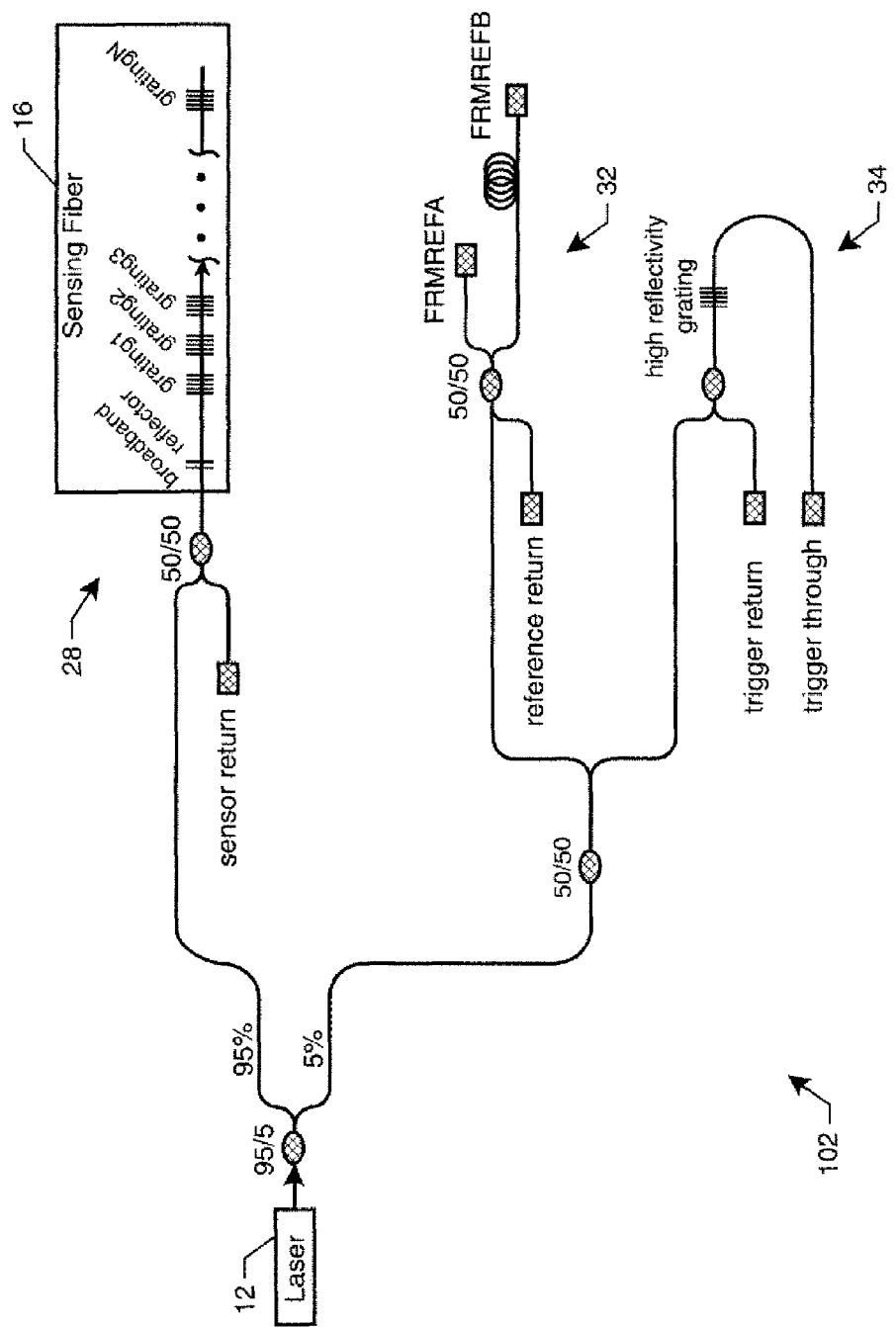
Figure 7:
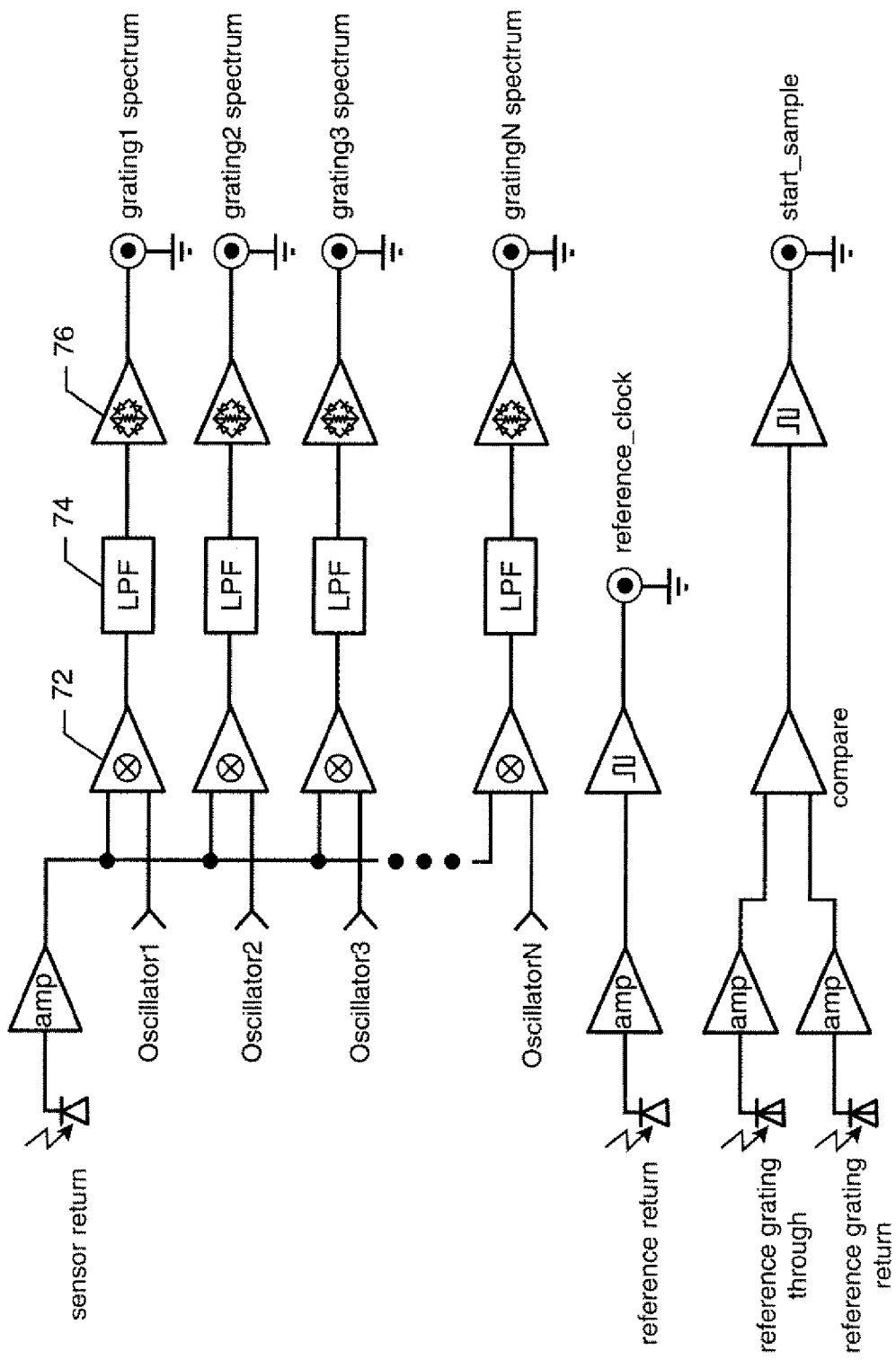
Figure 8:
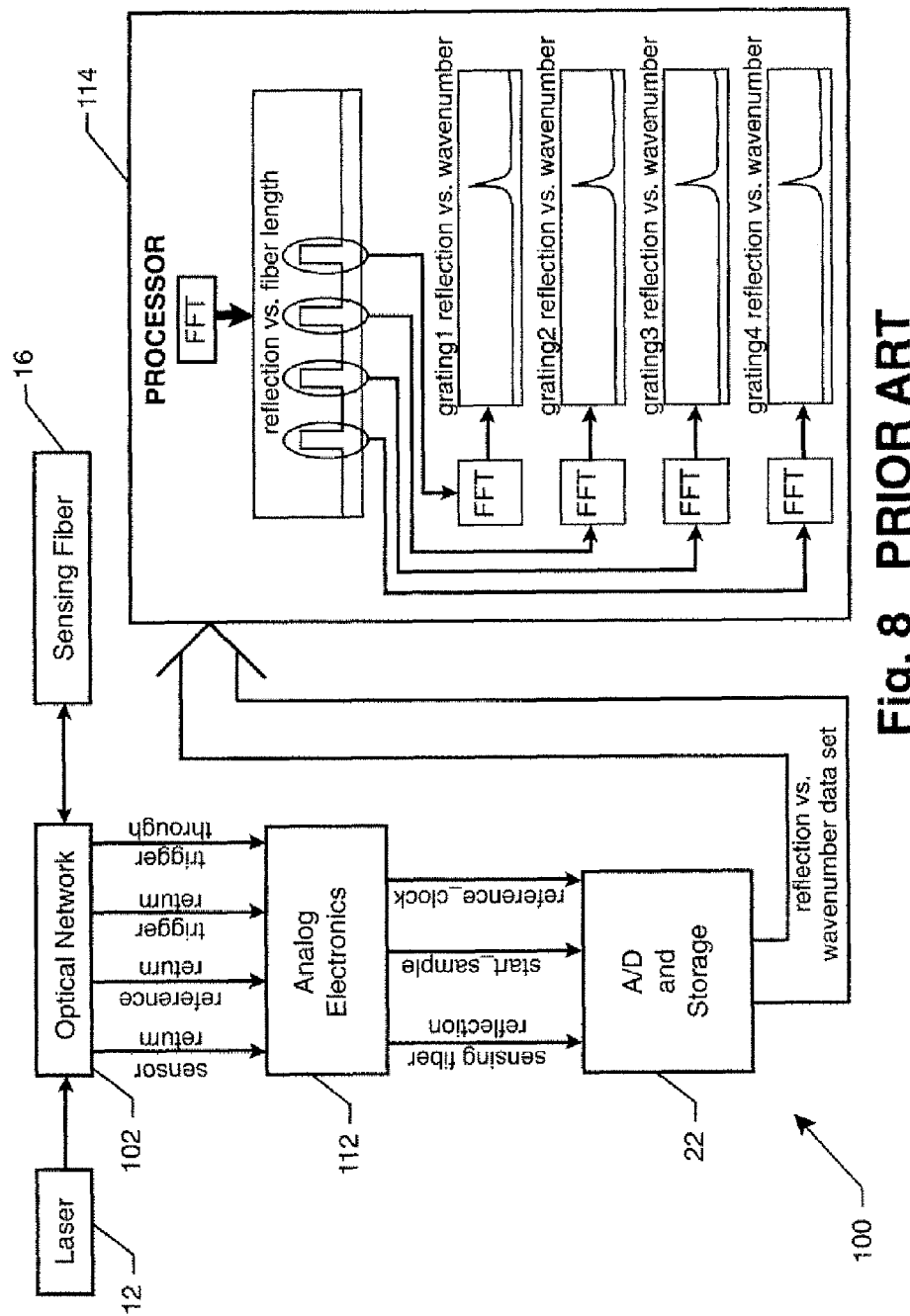

Having thus described the invention in general terms, reference will now be made to the accompanying drawings, which are not necessarily drawn to scale, and wherein:

FIG. 1 is a diagram of a system for determining a reflection wavelength of multiple low-reflectivity Bragg gratings in a sensing optical fiber having a broadband reflector and a plurality of the Bragg gratings at different distances from the broadband reflector along a length of the sensing optical fiber, in accordance with one embodiment of the invention;

FIG. 2 is a diagram of the optical network block of FIG. 1, in accordance with one embodiment of the invention;

FIG. 3 is a diagram of the analog electronics block of FIG. 1, in accordance with one embodiment of the invention;

FIG. 4 is a diagram of the digital electronics block of FIG. 1, in accordance with one embodiment of the invention;

FIG. 5 is a diagram of a system for determining a reflection wavelength of multiple low-reflectivity Bragg gratings in a sensing optical fiber having a broadband reflector and a plurality of the Bragg gratings at different distances from the broadband reflector along a length of the sensing optical fiber, in accordance with an alternative embodiment of the invention;

FIG. 6 is a diagram of the optical network block of FIG. 5, in accordance with one embodiment of the invention;

FIG. 7 is a diagram of the analog electronics block of FIG. 5, in accordance with one embodiment of the invention; and FIG. 8 is a diagram of a prior art system for determining a reflection wavelength of multiple low-reflectivity Bragg gratings in a sensing optical fiber,

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As in traditional OFDR systems and methods, embodiments of the present invention are capable of determining the spectra and/or peak reflection wavelengths of multiple Bragg gratings on a single sensing optical fiber. The sensing fiber comprises an inline partial broad band reflector and any number of Bragg gratings distributed along the fiber. When the source laser is swept in wavelength, this sensing fiber arrangement causes the reflection amplitude spectra of each Bragg grating sensor to amplitude modulate an interferometer beat frequency corresponding to the distance of each Bragg grating sensor from the broadband reflector along the length of the sensing optical fiber. Unlike traditional OFDR systems and methods, the system and method of embodiments of the present invention make use of a plurality of frequency generators. One frequency generator is provided for each Bragg grating, and each frequency generator produces a signal having a frequency corresponding to an interferometer frequency of a different one of the plurality of Bragg gratings. In one embodiment of the invention, the frequency generators are provided by an additional fiber optic networks termed an "oscillator" fiber network (each separate section of the network is termed an "oscillator"), that is coupled to the source laser. The oscillator network comprises a plurality of individual fiber optic interferometers (described in more detail below), one for each Bragg grating sensor and each matching the interferometer length between one of the Bragg grating sensors and the broadband reflector in the sensing fiber. The return from the sensing fiber and the returns from each individual oscillator interferometer are detected by individual photo-detectors and amplified. When the laser is frequency swept, the interferometer beat frequencies of the Bragg grating sensors each has a matching oscillator interferometer beat frequency. The detected output of the oscillator interferometer amplifiers are coupled with the detected output of the sensing fiber amplifier through electronic analog demodulation circuitry. Any known demodulation technique may be used. In one exemplary embodiment, the demodulation circuitry comprises an analog multiplier or mixer and a low pass filter. Because the oscillator interferometers match the lengths of individual Bragg grating sensor length interferometers, the spectrum of each sensor is multiplied, or mixed, down into the DC frequency range in the time domain at the output of each multiplier. A low pass filter module on the output of each multiplier module filters out other Bragg grating spectra and other information not pertaining to the particular Bragg grating sensor that is associated with each demodulator's input oscillator frequency. In this arrangement, each demodulation segment outputs the wavelength reflection spectrum of a Bragg grating sensor as the laser is wavelength swept. To determine reflection wavelength, the output spectra of each demodulator are subjected to peak detection circuitry, such as simple threshold detection or otherwise. A laser wavenumber detection element is configured to determine a wavenumber of the laser when peaks are detected. The laser wavenumber detection element may comprise a reference interferometer, a digital counting circuit, and a plurality of registers. The reference interferometer, which is used in the traditional OFDR technology, is used to provide a wavenumber "counting" signal. Because the reference interferometer length is calibrated, the wavenumber period of the fringes of the reference interferometer are known, which enables the reference signal to drive a digital counting circuit whose digital output can be stored in registers when triggered by the peak detection circuitry. The counter is disabled until a pulse from a "trigger" network (the wavelength reference grating fiber described below) enables counting. The trigger network contains a high reflectivity fiber Bragg grating whose reflected and transmitted optical power is detected, amplified, and compared to produce a digital "low" when not reflecting and a digital "high" when reflecting. In this configuration, the counter is enabled at a reliable, repeatable wavenumber, and the counter module provides a digital encoding of the wavenumber as the laser wavelength is swept. At the end of each sweep of the laser, each register contains the digitally encoded reflection wavenumber of each grating. To determine strain, minimal logistical hardware is needed to compare measured wavenumber values (i.e., when a peak is detected) to zero-strain, baseline wavenumber values.

Referring now to FIG. 1, a diagram of a system for determining a reflection wavelength of multiple low-reflectivity Bragg gratings in a sensing optical fiber having a broadband reflector and a plurality of the Bragg gratings at different distances from the broadband reflector along a length of the sensing optical fiber is illustrated, in accordance with one embodiment of the invention. The system 10 comprises a source laser 12, an optical fiber network 14 (described in more detail in conjunction with FIG. 2), a sensing fiber 16, analog electronics 18 (described in more detail in conjunction with FIG. 3), peak detection electronics 20, A/D sampling and storage hardware/software 22, and digital electronics 24 (described in more detail in conjunction with FIG. 4). The sensing fiber, as disclosed in Froggatt, comprises a partial inline broad band reflector, such as a Titanium Oxide plated fusion splice, coupled to a fiber containing the Bragg gratings at known distances from the broadband reflector. The source laser 12 for the system is generally a high-coherence, monotonically wavelength sweeping, continuous output, mode-hop free, fiber-coupled laser. As can be seen in FIG. 2, the optical network splits the optical power from the source laser and couples it to four sections. The laser output is first directed by a 95/5 coupler 26, which directs 95% of the optical power to the sensing section of the network. The other 5% of optical power is equally coupled to a reference interferometer 32, several oscillator interferometers 30, and a wavelength reference grating fiber 34.

The 95% of the optical power that is directed to the sensing section 28 is first directed through a one-by-two 50/50 coupler 26. Coupler 26 directs optical power to the sensing fiber 16 and couples the reflected optical power from the sensing fiber back through the coupler and to a photo-detector 38. The signal from the photo-detector 38 provides a "sensor return" signal to the analog electronics (as discussed in conjunction with FIG. 3). Optical power is directed to the reference interferometer 32 through a two-by-two 50/50 coupler 40. The 50/50 coupler 40 directs optical power through two fibers 42, 44 of different lengths, both terminated with a Faraday rotator mirror (FRMREFA and FRMREFB respectively), and couple the reflected optical power from the two lengths hack through the coupler and onto a photo-detector 46. The signal from the photo-detector 46 provides a "reference return" signal to the analog electronics (as discussed in conjunction with FIG. 3). The reference interferometer 32, whose length is arbitrary, is used to produce an optical signal which is detected and converted to an electronic signal, and the electronic signal is used to drive the clocking of a digital counter 80 (shown in FIG.4) and, optionally, to drive the sampling of an A/D converter 22 (shown in FIG. 1) to record the spectra of each grating if so desired by the system user.

Optical power is directed to each of a plurality of "oscillator" interferometers 30 through a 50/50 coupler 48 (for simplification purposes, the components of only one of the oscillator interferometers are labeled). The 50/50 coupler 48 directs optical power through two fibers 50, 52 of different lengths, both terminated with a Faraday rotator mirror (FRM1A and FRM1B respectively), and couple the reflected optical power from the two lengths back through the coupler and onto a photo-detector 54. The signal from the photo-detector 54 provides an "oscillator" signal to the analog electronics (as discussed in conjunction with FIG. 3). For each interferometer, the difference in length between each of the two fibers is equal to the fiber length difference between the broadband reflector and one of the gratings in the sensing fiber. So, for example, if there were five gratings in the sensing fiber and their distances from the broadband reflector were 1, 2, 3, 4, and 5 meters, respectively, there would be five interferometers in the optical network whose fiber length differences are 1, 2, 3, 4, and 5 meters.

The wavelength reference grating fiber 34 comprises a high reflectivity grating with a calibrated reflection wavelength. It is fusion spliced to a coupler 56 in such a way that reflected and transmitted optical power are detected at photo detectors 58, 60, respectively, and amplified for comparison. As discussed in more detail below, the wavelength reference (rating fiber provides the digital pulse to start the digital counter and the clocking of the A/D converters for spectral sampling. This serves as a calibrated reference for each laser scan.

The interrogation of the sensing fiber begins with the laser emitting at the lower wavelength of the laser's wavelength scanning range. The laser then scans upward in wavelength and stops at the high wavelength of the wavelength scanning range. The laser has a monotonic sweeping characteristic (i.e., as the wavelength is being swept, there is substantially no jitter or backlash or any other type of behavior that might cause a negative sweeping derivative during scanning). The laser is also a continuous output laser in which there is substantially no dropout of power during the wavelength sweep. The optical output of the laser is coupled directly to the optical network, as described above. As the laser sweeps wavelength, the gratings reflect a particular wavelength of optical power according to their own individual strain conditions. When a grating is reflecting optical power, an interferometer condition is established between the orating and the broadband reflector. The reflection spectrum will amplitude modulate the sinusoidal interference output of the broadband reflector-grating pair. In this way, the reflection spectrum of each grating is returned through the coupler as an amplitude-modulated sinusoidal optical signal whose frequency is dependant on the length of fiber between the broadband reflector and each grating. As the laser is wavelength-swept, each oscillator interferometer creates an optical "oscillator" signal having an interferometer frequency closely matching the interferometer frequency of one of the gratings in the sensing fiber.

The reflected power from the sensing fiber, the reflected power from the oscillator interferometers, the reflected power from the reference interferometer, and the transmitted and reflected optical power from the wavelength reference grating are all connected to the analog electronics module 18 for detection and amplification, as illustrated in FIG. 3. Each optical signal is connected to an individual photodetector 62 and amplifier 64 (for simplification purposes, only one photodetector and amplifier are labeled). The "reference return" optical power is detected, amplified, and converted to a digital square wave circuit 66 to produce the digital "reference_clock" signal. As described in Froggatt, this "reference_clock" signal is a digital clocking type signal that can be used to drive A/D conversion and sampling. This signal is also used to drive a digital counter, described later. The "reference grating through" and "reference grating return" optical signals are detected, amplified, and connected to a comparator circuit 68 and a digital square wave circuit 70 for conversion to a digital signal. The "reference grating through" signal is connected to the negative input of the comparator while the "reference grating return" signal is connected to the positive input of the comparator. This configuration yields a digital "start_sample" signal that is a digital "high" when the reference grating is reflecting and is digital "low" when the reference grating is not reflecting. This signal is used to trigger the start of an A/D conversion and sample operation and is also used to trigger the start of the digital counting inside the "digital electronics" module 24 (as described in more detail below). In the embodiment of FIG. 3, each oscillator interferometer signal has an associated demodulation circuit comprising a multiplier 72 and a low-pass filter 74, and each demodulation circuit output is connected to a corresponding rectifier circuit 76 (for simplification purposes, only one of each of the multiplier, low-pass filter, and rectifier are labeled) (the rectifier performs part of the peak detection function, discussed below). The sensing fiber return signal ("sensor return") is also input to each multiplier, as shown in FIG. 3. The output of each multiplier is low-pass filtered and rectified to yield the spectrum of the sensing fiber Bragg grating which is located at a distance from the broad band reflector which corresponds to its respective oscillator interferometer length. Because each demodulation circuit has a different oscillator interferometer signal at its oscillator input which corresponds to a grating location in the sensing fiber, each demodulation circuit will "tune" to a different grating and demodulate a specific grating reflection spectrum to near DC frequencies on its output. A low pass filter circuit on each multiplier output filters out any information not near DC frequencies, and a rectifier conditions the signal for peak detection. This configuration yields multiple demodulation circuit outputs, each containing the reflection spectrum of a different Bragg grating. The outputs of the demodulation circuits ("grating 1 spectrum," "grating 2 spectrum," "grating 3 spectrum," . . . "grating N spectrum") are connected to a peak detection module 20, where the signals are edge- or peak-detected to produce digital trigger signals to trigger the registering of the digital counter values inside the digital electronics (as discussed in more detail below).

The outputs of the demodulation circuits ("grating 1 spectrum," "grating 2 spectrum," "grating 3 spectrum," . . . "grating N spectrum") may also be connected to an A/D module 22 for sampling/storage in the fashion previously outlined by Froggatt, if so desired. It is noted, however, that the purpose of the present invention is to yield measurement data without the need for sampling signals and performing digital processing. The sampling methodology of Froggatt is included here to illustrate that embodiments of the present invention do not eliminate the capability to perform Froggatt's sampling technique. The start_sample signal and the reference_clock signal may be connected to the A/D & Storage module 22 in order to perform this task. As discussed in Froggatt, the A/D conversion is initiated by the start_sample signal transitioning to digital "high." The start_sample signal is digital "high" when the laser sweeps through the predetermined reflection wavelength of the wavelength reference grating fiber 34 (i.e., when the laser is emitting at the same wavelength as the predetermined reflection wavelength of the reference grating fiber). The wavelength reference grating fiber 34 is carefully calibrated (e.g., with National Institute of Standards and Technology traceability) such that the reflection wavelength is known and repeatable. This enables the initiation of the A/D conversion to be repeatable at the same laser wavelength over multiple scans of the laser. The reference_clock signal has a period directly related to the length of the reference interferometer 32. The period is represented as $1/(2nL_{ref})$, where n is the index of refraction of the fiber making up the reference interferometer and $L_{ref}$ is the length difference, in meters, of the reference interferometer. The units of the phase are meters$^{-1}$. This relationship maps the basis of the sampled set into the wavenumber domain, with the basis zero point being 1/(reference grating trigger wavelength), and each sample being $1/(2nL_{ref})$ apart. Sampling each demodulation circuit output in this way yields the relative optical reflection amplitude versus wavenumber for each grating in the sensing fiber.

As mentioned above, the outputs of the demodulation circuits ("grating 1 spectrum," "grating 2 spectrum," "grating 3 spectrum," . . . "grating N spectrum") are connected to the peak detection electronics module 20. Each output spectrum is either peak-detected or edge-detected as the source laser is wavelength-swept in order to produce a digital signal that is "high" when the peak is detected (these peak detection signals are labeled in FIGS. 1 and 4 as grating1_peak_detect, grating2_peak_detect, grating3_peak_detect, . . . gratingN_peak_detect).

As illustrated in FIGS. 1 and 4, the inputs to the digital electronics module 24 are: start_sample, reference_clock, and grating1_peak_detect, grating2_peak_detect, grating3_peak_detect, . . . gratingN_peak_detect. When the source laser 12 sweeps wavelength, a start_sample "high" signal resets the counter 80 and the registers 82 (for simplification purposes, only one is labeled) when the wavelength of the laser crosses through the reference grating reflection wavelength. Each Bragg grating of the sensing fiber has its own digital register that is controlled by its corresponding gratingX_peak_detect signal. When the start_sample signal goes "low" (because the laser wavelength no longer equals the reference grating reflection wavelength), the counter will count as driven by reference_clock. As the peaks of the sensing fiber gratings are detected, the grating 1_peak_detect, grating2_peak_detect, grating3_peak_detect, . . . gratingN_peak_detect signals switch to "high" and the registers of the respective gratings store the digital counter output.

Other inputs, outputs, and components not shown may include, but are not limited to, signals to indicate the scanning direction of the laser (increasing or decreasing wavelength), connections for extracting the digital information stored in the registers, hardware to eliminate timing conflicts between the digital counter and the registers, and hardware for comparing measured values to baseline values to yield absolute results.

The source laser may be any laser whose characteristics are: (1) monotonic in wavelength tuning (up or down); (2) continuous output; (3) fiber coupled or capable of being fiber coupled; (4) mode-hop free during tuning; and (5) highly coherent (i.e., enough coherence to provide adequate interference for the longest interferometer in the optical network). Some lasers have a self-scanning control capability in which the laser will scan up and down in a wavelength range entered by the user, while others require a control input to initiate a wavelength sweep. The latter typically requires that the user or a control processor program the laser as to the wavelength at which this line will transition to "high". Some lasers have a digital wavelength output line which can be used in place of the start_sample digital line used to clear the digital counter and grating registers at the start of a measurement. The connections from optical module to optical module can be accomplished through fusion splicing, connectors, or any other means in which back reflections do not cause significant signal errors. The sensing fiber can have any number of gratings at any distance from the broadband reflector so long as sufficient interferometer behavior exists. The distance between gratings on the sensing fiber can be as small as needed so long as the low-pass filter circuitry in the detection and analog electronics module can still sufficiently suppress unwanted "other" grating spectra. The sensing fiber does not have to use Bragg gratings. The invention described here can be used to determine the spectrum of any reflective artifact or otherwise in optical fiber. The interferometric signal formations in the optical network can be accomplished a variety of ways, including, but not limited to, using polarization-maintaining fiber in place of circular-core fiber, using a two-coupler configuration, or on a substrate as would be done for miniaturization of the optical network. The sensing fiber can consists of multi-core fiber. Polarization-maintaining fiber may be used anywhere in the fiber optic network or sensing fiber. The optical power detection and electronic amplification methods are not specific to this invention and may be accomplished using any known means. The mixing/multiplying circuitry and low-pass filter methods are not specific to this invention and may be accomplished using any known means. The digital counting and register configurations are not specific to this invention and may be accomplished using any known means. Although not illustrated, power supply and associated noise-reduction hardware are generally required in any electronics application. Also not illustrated is hardware for extracting the stored counter values from the grating registers or associated processing hardware to convert these digitally stored values into a wavenumber measurement.

Referring now to FIGS. 5-7, a system for determining a reflection wavelength of multiple low-reflectivity Bragg gratings in a sensing optical fiber is illustrated, in accordance with an alternative embodiment of the invention. This alternate embodiment eliminates the need for several extra "oscillator" interferometers by using a plurality of frequency synthesizers (one for each Bragg grating) to generate the oscillator signals. Using electronic frequency synthesizers in place of optical interferometers may lower system production costs and allow for a smaller system package size. Also, frequency synthesizers are actively programmable, in contrast to the optical interferometers which are constructed to specific lengths and are non-adjustable once constructed. Using programmable synthesizers in place of all-optical interferometer assemblies allows the system to adapt to interchangeable sensing fibers, which can have sensors in differing locations from fiber to fiber. The system 100 of FIG. 5 comprises electronic frequency synthesizers 104. The optical network 102 and the analog electronics block 106 also vary from the system of FIG. 1, as discussed further below. The digital reference_clock signal (from the reference interferometer 32) is connected to each frequency synthesizer and serves as the master clock for each synthesizer. There is one frequency synthesizer for each Bragg grating to be measured. The frequency synthesizers output sinusoidal signals, labeled oscillator 1, oscillator 2, oscillator 3, . . . oscillator N, at their respective programmed frequencies based on the master clock input. As an example, the AD9832 frequency synthesizer, produced by Analog Devices, Inc., can output one of $2^{32}$ (more than 4 billion) different frequencies, up to the master clock frequency. Because the frequency synthesizer derives its output from the master clock input, and because the reference_clock signal provides the master clock input, the frequency synthesizers will adjust the oscillator signal frequencies automatically in the case of a varying laser wavelength sweep speed. If the laser wavelength sweep characteristic is sufficiently constant, the reference_clock signal does not need to be used as the master clock input. In such a case, a simple time-based signal, such as one from a crystal oscillator, may be used in its place. Also, if one sensing fiber is replaced by another with Bragg grating sensors in different locations, the frequency synthesizers can be easily adjusted by the system control processor (not illustrated). The required oscillator frequencies are calculated in terms of distance. If the reference-clock signal is derived from a reference interferometer that is 30 meters long, and a Bragg grating is 5 meters along the sensing fiber from the broad-band reflector, then the output of the frequency synthesizer to demodulate that grating would have to be ⅙th (i.e., 5/30) the frequency of reference_clock.

The fiber optic network of this alternative embodiment is illustrated in FIG. 6. As can be seen in FIG. 6, the fiber optic network of the alternative embodiment is very similar to that of the embodiment of FIGS. 1-4 in that the source laser 12 the sensing fiber 28, the reference interferometer 32, and the wavelength reference grating fiber 34 are the same. However, the fiber optic network of FIG. 6 omits the oscillator interferometers (element 30 of FIG. 2) because their function is replaced by frequency synthesizers. The analog electronics block of this alternative embodiment is illustrated in FIG. 7. As can be seen in FIG. 7, the photo-detectors (element 62 of FIG. 3) and associated amplifiers (element 64 of FIG. 3) for the oscillator optical network legs are eliminated and instead, the oscillator inputs to the demodulation modules come from the frequency synthesizers directly as electrical signals. The rest of the electronics of FIG. 3 remain unchanged in the alternative embodiment of FIGS. 5-7.

To further illustrate the improvements of the present invention over the prior art, FIG. 8 illustrates a prior art OFDR system for determining a reflection wavelength of multiple low-reflectivity Bragg gratings in a sensing optical fiber. The prior art system 110 of FIG. 8 comprises a source laser 12, an optical network 102, a sensing fiber 16, analog electronics 112, A/D sampling and storage hardware/software 22, and a processor 114. The source laser 12 and the sensing fiber 16 of the prior art system are the same as described above in conjunction with embodiments of the present invention. The optical network 102 of the prior art system is the same as in the embodiment of the present application illustrated in FIG. 6. The analog electronics 112 of the prior art system comprises the same "start_sample" circuitry and "reference_clock" circuitry as in the embodiments of the present invention illustrated in FIGS. 3 and 7, thereby providing a "start_sample" signal and a "reference_clock" signal to the A/D sampling and storage hardware/software 22 as illustrated in FIG. 8. The analog electronics 112 further comprise an optical detector and amplifier to receive and amplify the reflection from the sensing fiber, thereby providing a "sensing fiber reflection" signal to the A/D sampling and storage hardware/software 22 as illustrated in FIG. 8.

In the prior art of FIG. 8, the A/D converter is used to sample a data set during a laser sweep. This data set comprises reflection versus wavenumber from the sensing fiber. To obtain grating reflection wavelength, the data set must be Fourier Transformed (using, for example, Fast Fourier Transform) to determine reflection versus length in the sensing fiber. The FFT is performed in the processor 114 of FIG. 8. Then, individual data sets from that result must be Fourier Transformed to determine the reflection spectrum versus wavenumber for each grating. Then, a peak-detection algorithm must be implemented in the processor to determine the peak reflection wavenumber for each grating. All of these transforms are performed in the processor 114, which takes a finite amount of time. Regardless of the speed of the processor, the prior art method always includes data processing and the time delays inherent in such data processing. The first FFT in the prior art method is typically a minimum 250,000 points long, and the time required for the processor to accomplish that transform is significant. In contrast, embodiments of the present invention eliminate the Fourier transforms, thus eliminating the time delay due to processing.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed as new and desired to be secured by Letters Patent of the United States is:

1. A system for determining a reflection wavelength of multiple low-reflectivity Bragg gratings in a sensing optical fiber having a broadband reflector and a plurality of the Bragg gratings at different distances from the broadband reflector along a length of the sensing optical fiber, the system comprising:
    a source laser coupled to the sensing optical fiber;
    an optical detector coupled to the sensing optical fiber and configured to detect a reflected signal from the sensing optical fiber;
    a plurality of frequency generators, each frequency generator configured to generate a signal having a frequency corresponding to an interferometer frequency of a different one of the plurality of Bragg gratings;
    a plurality of demodulation elements, each demodulation element coupled to the optical detector and to a different one of the plurality of frequency generators, each demodulation element configured to combine the signal produced by a different one of the plurality of frequency generators with the detected signal from the sensing optical fiber;
    a plurality of peak detectors, each peak detector coupled to a different one of the demodulation elements and configured to detect a peak of the combined signal from a different one of the demodulation elements; and
    a laser wavenumber detection element coupled to the peak detectors and configured to determine a wavenumber of the laser when any of the peak detectors detects a peak.

2. The system of claim 1, wherein the plurality of frequency generators each comprise a frequency synthesizer.

3. The system of claim 1, wherein the plurality of frequency generators each comprise an optical fiber interferometer, each interferometer comprising two lengths of optical fiber having a difference in length substantially equal to the distance between the broadband reflector and a different one of the plurality of Bragg gratings.

4. The system of claim 1, wherein the laser wavenumber detection element comprises:
    a reference optical fiber network coupled to the source laser and configured to provide a wavenumber counting signal;
    a calibrated optical fiber network configured to reflect light from the source laser when the source laser is emitting light at a predetermined frequency;
    a counter coupled to the reference optical fiber network and the calibrated optical fiber network, the counter being, clocked by the wavenumber counting signal and triggered by the reflection of light from the calibrated optical fiber network; and
    a plurality of registers, each register configured to capture and store an output value from the counter upon when a different one of the peak detectors detects a peak.

5. The system of claim 1, wherein the source laser comprises a high coherence, monotonically wavelength sweeping, continuous output, mode-hop free, fiber-coupled laser.

6. The system of claim 1, wherein each demodulation element comprises an analog multiplier and a low-pass filter.

7. The system of claim 1, wherein each demodulation element comprises an analog mixer and a low-pass filter.

8. A method for determining a reflection wavelength of multiple low-reflectivity Bragg gratings in a sensing optical fiber having a broadband reflector and a plurality of the Bragg gratings at different distances from the broadband reflector along a length of the sensing optical fiber, the method comprising the steps of:

providing a source laser coupled to the sensing optical cable;

providing an optical detector coupled to the sensing optical fiber and configured to detect a reflected signal from the sensing optical fiber;

providing a plurality of frequency generators, each frequency generator configured to generate a signal having a frequency corresponding to an interferometer frequency of a different one of the plurality of Bragg gratings;

providing a plurality of demodulation elements, each demodulation element coupled to the optical detector and to a different one of the plurality of frequency generators, each demodulation element configured to combine the signal produced by a different one of the plurality of frequency generators with the detected signal from the sensing optical fiber;

providing a plurality of peak detectors, each peak detector coupled to a different one of the demodulation elements and configured to detect a peak of the combined signal from a different one of the demodulation elements; and providing a laser wavenumber detection element coupled to the peak detectors and configured to determine a wavenumber of the laser when any of the peak detectors detects a peak.

9. The method of claim 8, wherein the plurality of frequency generators each comprise a frequency synthesizer.

10. The method of claim 8, wherein the plurality of frequency generators each comprise an optical fiber interferometer, each interferometer comprising two lengths of optical fiber having a difference in length substantially equal to the distance between the broadband reflector and a different one of the plurality of Bragg gratings.

11. The method of claim 8, wherein the laser wavenumber detection element comprises:

a reference optical fiber network coupled to the source laser and configured to provide a wavenumber counting signal;

a calibrated optical fiber network configured to reflect light from the source laser when the source laser is emitting light at a predetermined frequency;

a counter coupled to the reference optical fiber network and the calibrated optical fiber network, the counter being clocked by the wavenumber counting signal and triggered by the reflection of light from the calibrated optical fiber network; and a plurality of registers, each register configured to capture and store an output value from the counter upon when a different one of the peak detectors detects a peak.

12. The method of claim 8, wherein the source laser comprises a high coherence, monotonically wavelength sweeping, continuous output, mode-hop free, fiber-coupled laser.

13. The method of claim 8, wherein each demodulation element comprises an analog multiplier and a low-pass filter.

14. The method of claim 8, wherein each demodulation element comprises an analog mixer and a low-pass filter.

* * * * *